United States Patent [19]

Senanayake et al.

[11] Patent Number: 6,013,830

[45] Date of Patent: Jan. 11, 2000

[54] ASYMMETRIC GRIGNARD SYNTHESIS WITH CYCLIC 1,2 AMINOALCOHOLS

[75] Inventors: Chris Hugh Senanayake; Roger P. Bakale, both of Shrewsbury; Qun Kevin Fang, Wellesley; Paul Timothy Grover, Marlborough; Donald L. Heefner, Hudson; Richard F. Rossi, Norton; Stephen Alan Wald, Sudbury, all of Mass.

[73] Assignee: Sepracor Inc., Malborough, Mass.

[21] Appl. No.: 09/050,825

[22] Filed: Mar. 30, 1998

[51] Int. Cl.[7] ......................... C07C 69/76; C07D 263/54
[52] U.S. Cl. ............................. 560/58; 548/217; 548/498
[58] Field of Search .................................................. 560/58

[56] References Cited

U.S. PATENT DOCUMENTS 5,516,943  5/1996  Gao et al. ................................. 564/444

FOREIGN PATENT DOCUMENTS 4142190    6/1993   Germany .
WO9623492  8/1996   WIPO .
WO9636584  11/1996  WIPO .

OTHER PUBLICATIONS

Hamon et al. "Asymmetric Syntheses with a new Optically Active . . . " *Tetrahedron 42,* 9593–9604 (1993).
Boireau et al. "Synthese D'α–Hydroxyacides Optiquement Actifs Par Addition . . . " *Tetrahedron 45,* 5837 (1989).
Basavaiah et al. "New Cyclohexyl–Based Chiral Auxiliaries: Enantioselective . . . " *Tetrahedron 51,* 12169–78 (1995).
Boireau et al. "Application De Reactions D'Hydroalumination En Synthese . . . " *Tetrahedron Letters 26,* 4181–4182 (1985).
Boireau et al. "Addition Diastereoselective D'Organozinciques Sur Le . . . " *Tetrahedron Letters 29,* 215–2176 (1988).
Basavaiah et al. "Enantioselective Synthesis of α– and β–Hydroxy Acids Using . . . " *Tetrahedron Letters 32,* 3417–3420 (1991).
Tamai et al. "Reinvestigation of the Addition of Methylmagnesium Iodide to the . . . " *Chemistry Letters,* 1135–1136 (1989).
Kawanami et al. "Diastereoselective Addition of Organometallics to N– (α– Ketoacyl)–. . . " *Chemistry Letters,* 2063–2066 (1989).
Akiyama et al. "Diastereolselective Addition of Organometallics to α–Keto Esters Bearing . . . " *Chemistry Letters,* 447–450 (1992).
Ghosh et al. "Highly Stereoselective Reduction of α–Keto Esters: Utility of Cis–1–. . . " *Tetrahedron Letters* 6811–6814 (1995).

Basavaiah et al. "trans–2–Phenoxycylcohexan–1–OL as New Chiral Auxiliary: Synthesis . . . " *Synthetic Communications 22,* 941–47 (1992).
Solladie–Cavallo et al. "Diastereoselective Reduction of an α–Keto–Ester Derived . . . " *Tetrahedron: Asymmetry 2,* 1165–1171 (1991).
Tamai et al. "Investigation of the Diastereoselectivity in the Addition of Organometallics . . . " *J. Chem. Soc. Perkin Trans. 1,* 439–445 (1994).
Esser et al. "trans–2–tert–Butylcyclohexanol, A simple Selectively Optimized . . . " *Angew. Chem. Int. Ed. Engl. 31,* 1190–92 (1992).
Senanayake et al. "Regio– and Stereocontrolled Syntheses of Cyclic Chiral cis–Amino . . . " *Tetrahedron Letters 36,* 7615–7618 (1995).
Armstrong et al. "Stereocontrolled Addition of Chiral, Non–Racemic Amide Homoenolates . . . " *Tetrahedron Letters 44,* 6599–6602 (1992).
Askin et al. "Highly Diastereoselective Alkylations of Chiral Amide Enolates: New Routes . . . " *J. Org. Chem. 57,* 2772–2773 (1992).

*Primary Examiner*—Johann Richter
*Assistant Examiner*—Ebenezer Sackey
*Attorney, Agent, or Firm*—Heslin & Rothenberg, P.C.

[57] ABSTRACT

Processes for preparing a single enantiomer of an α,α-disubstituted-α-hydroxy acetic acid, especially cyclohexylphenylglycolic acid (CHPGA), is disclosed. The processes employ cyclic 1,2-aminoalcohols as chiral auxiliaries by forming diastereomeric esters of aminoalcohols or diastereomeric amides of oxazolidines.

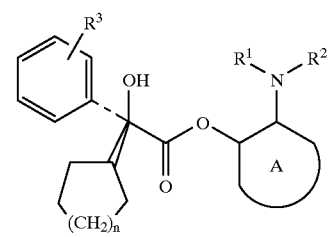

and

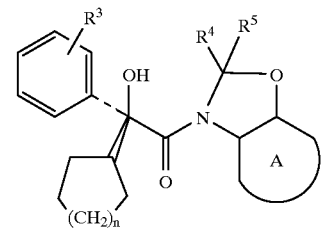

Intermediates useful in the process are also disclosed.

11 Claims, No Drawings

ASYMMETRIC GRIGNARD SYNTHESIS WITH CYCLIC 1,2 AMINOALCOHOLS

FIELD OF THE INVENTION

The present invention relates to chemical processes and to intermediates in those processes.

BACKGROUND OF THE INVENTION

α,α-Disubstituted-α-hydroxy acetic acids are starting materials and intermediates for manufacturing compounds that have important biological and therapeutic activities. Such compounds include, for example, oxybutynin, oxyphencyclimine, oxyphenonium bromide, oxypyrronium bromide, and oxysonium iodide, for which cyclohexylphenylglycolic acid (CHPGA) is of special interest.

Racemic CHPGA is generally prepared by one of two methods: (1) selective hydrogenation of phenyl mandelic acid or of phenyl mandelate esters, as shown in Scheme 1; or (2) cyclohexyl magnesium halide addition to phenylglyoxylate as shown in Scheme 2.

Scheme 1.

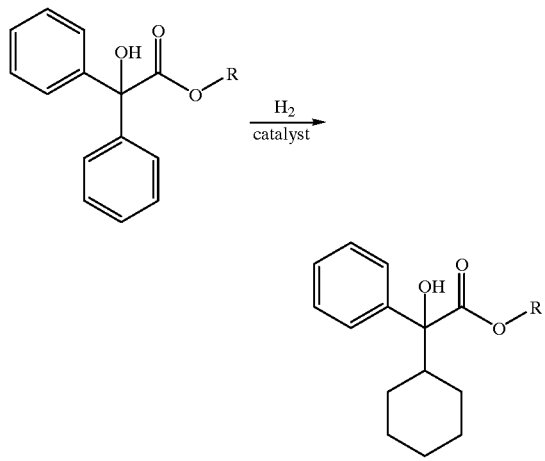

R is hydrogen or lower alkyl.

Scheme 2.

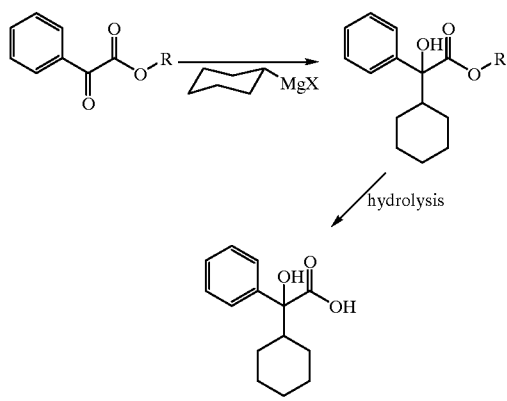

The synthesis of individual enantiomers of CHPGA has been approached along the lines of Scheme 2, by Grignard addition to a chiral auxiliary ester of glyoxylic acid to give a diastereomeric mixture of esters. In general, simple primary alkyl or phenyl Grignard (or alkyllithium) reagents were used for the addition, and the addition of inorganic salts (e.g. $ZnCl_2$) sometimes appeared to increase the diastereoselectivity of the products. As outlined in Scheme 3, the simple chiral ester wherein R* is the residue of a chiral alcohol, can be hydrolyzed to yield chiral CHPGA (R'=H), or directly converted to chiral drugs or drug candidates by trans-esterification (R'=acetate), for example by reaction with an amino alcohol side chain to prepare S-oxybutynin.

Scheme 3.

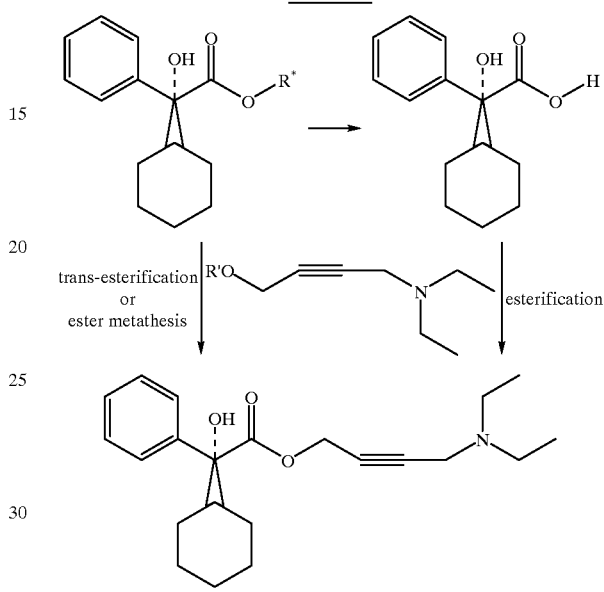

While these methods are adequate for many purposes, the chemical yields are in some cases poor, and the stereoselectivity is not always high. The chiral auxiliary reagents that give good yields and higher stereoselectivity are often quite expensive. There remains therefore a need for a highly stereoselective synthesis of CHPGA and related compounds that provides high chemical yields at lower cost.

SUMMARY OF THE INVENTION

This need is satisfied, the limitations of the prior art overcome, and other benefits realized in accordance with the principles of the present invention, which in one aspect relates to a process for the enantioselective synthesis of a chiral α-hydroxycarboxylate. The process comprises:

(a) reacting a prochiral α-ketocarboxylic acid with a single enantiomer of an N-substituted vicinal aminoalcohol of cyclopentane, cyclohexane, cycloheptane, indane, tetralin or benzosuberane to form an ester of the α-ketocarboxylic acid;

(b) reacting the ester with an excess of a Grignard reagent in an ethereal solvent at 20° to −78° C. to provide a reaction mixture containing a diastereomer of an α-hydroxycarboxylate ester;

(c) separating a single diastereomer of the α-hydroxycarboxylate ester from the reaction mixture; and, optionally, (d) hydrolyzing the α-hydroxycarboxylate ester to provide an α-hydroxycarboxylic acid or α-hydroxycarboxylate salt enriched in one enantiomer. A salt of zinc, cerium, titanium, iron or copper may be added to step (b). Separation of the single diastereomer of α-hydroxycarboxylate ester from the reaction mixture may be accomplished by fractional crystallization or chromatography. Hydrolysis may be carried out with aqueous alkali metal hydroxide or enzymatically. In one embodiment, the prochiral α-ketocarboxylic acid is reacted with a single enantiomer of a vicinal aminoalcohol by forming an acid chloride and reacting the acid chloride with the aminoalcohol. In another embodiment, the prochiral α-ketocarboxylic acid is reacted with a single enantiomer of a vicinal aminoalcohol by activation with a carbodiimide. In preferred embodiments, the prochiral α-ketocarboxylic acid is either phenylglyoxylic acid or cyclohexylglyoxylic acid and the single enantiomer of a vicinal aminoalcohol is a single enantiomer of 2-tosylamino-1-cyclopentanol, 2-tosylamino-1-cyclohexanol, 1-tosylamino-2-indanol, 2-tosylamino-2-phenyl-1-cyclohexanol or 1-dimethylamino-2-indanol.

In another aspect, the invention relates to a process for the enantioselective synthesis of a chiral α-hydroxycarboxylate comprising:

(a) reacting an acid chloride of a prochiral α-ketocarboxylic acid with a single enantiomer of a vicinal aminoalcohol of cyclopentane, cyclohexane, cycloheptane, indane, tetralin or benzosuberane in the presence of an enol ether of a lower alkylketone or a dialkoxyalkane and strong organic acid or anhydrous Lewis acid catalyst to form a 2,2-dialkyl-1-glyoxylyloxazolidine;

(b) reacting the 2,2-dialkyl-1-glyoxylyloxazolidine with an excess of a Grignard reagent in an ethereal solvent at 20° to −78° C. to provide a reaction mixture containing a 2,2-dialkyl-1-(β-hydroxy-α-oxomethyl)oxazolidine;

(c) separating a single diastereomer of 2,2-dialkyl-1-(β-hydroxy-α-oxomethyl)oxazolidine from the reaction mixture; and (d) hydrolyzing the 2,2-dialkyl-1-(β-hydroxy-α-oxomethyl)oxazolidine to provide an α-hydroxycarboxylic acid or α-hydroxycarboxylate salt enriched in one enantiomer.

As before, a salt of zinc, cerium, titanium, iron or copper may be added to step (b). The hydrolysis of the oxazolidine may be carried out sequentially with aqueous mineral acid, followed by alkali metal hydroxide in a high boiling solvent or an enzyme in an aqueous medium. In preferred embodiments, the prochiral α-ketocarboxylic acid is either phenylglyoxylic acid or cyclohexylglyoxylic acid; the single enantiomer of a vicinal aminoalcohol is 2-amino-1-cyclopentanol, 2-amino-1-cyclohexanol or 1-amino-2-indanol; the enol ether is 2-methoxypropene; the ammonium salt catalyst is pyridinium toluenesulfonate; and the Grignard reagent is a cycloalkylmagnesium halide or a phenylmagnesium halide.

In another aspect, the invention relates to compounds useful as intermediates in the foregoing processes. In the following disclosure, the variables are defined when introduced and retain that definition throughout. The compounds useful as intermediates in the foregoing processes include compounds of formula IVa

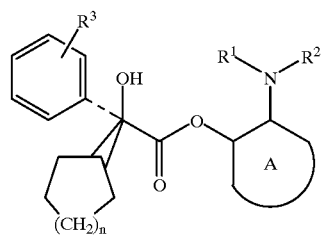

wherein $R^1$ is chosen from the group of alkyl, cycloalkyl, and arylsulfonyl;

$R^2$ is alkyl or cycloalkyl, or, when $R^1$ is arylsulfonyl, $R^2$ may additionally be hydrogen;

or together $R^1$ and $R^2$ alkylene,

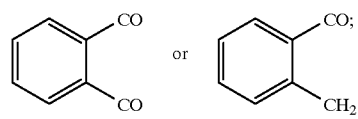

$R^3$ is one or more substituents chosen independently from the group of hydrogen, alkyl, alkoxyl and halo;

n is 1, 2, 3 or 4; and

A is a cyclic residue chosen from the group of cyclopentane, cyclohexane, cycloheptane, indane, tetralin or benzosuberane.

They also include compounds of formula III

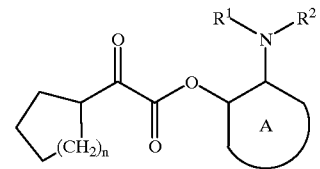

wherein A has a configuration such that the compounds are either pure enantiomers or predominantly one enantiomer. Preferred subgenera include those in which $R^3$ is hydrogen; those in which A is cyclopentane, cyclohexane, tetralin, or most preferably indane; those in which $R^1$ is methyl or toluenesulfonyl and $R^2$ is hydrogen or methyl; and those in which $R^1$ is toluenesulfonyl and $R^2$ is hydrogen. Particularly preferred are compounds of formulae

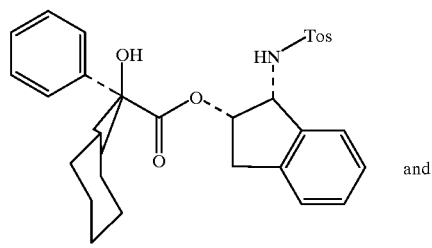

and

-continued

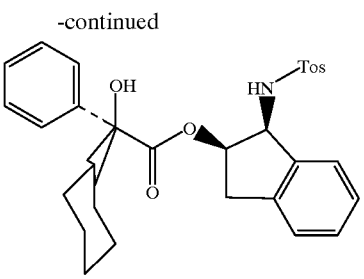

Other compounds useful as intermediates include compounds of formula VIIIa, VIIa and VIb:

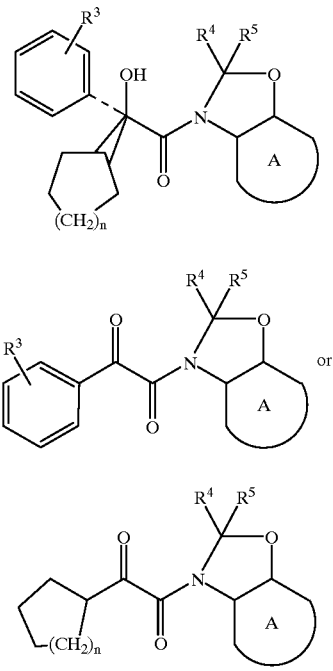

wherein $R^4$ and $R^5$ are lower alkyl or, taken together, $R^4$ and $R^5$ are a carbonyl function. Preferred compounds are those in which $R^3$ is hydrogen; in which A is cyclopentane, cyclohexane, tetralin, or most preferably, indane; and in which $R^4$ and $R^5$ are both methyl.

DETAILED DESCRIPTION

The graphic representations of racemic, ambiscalemic and scalemic or enantiomerically pure compounds used herein are taken from Maehr *J. Chem. Ed.* 62, 114–120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but denoting racemic character; and wedge outlines and dotted or broken lines denote enantiomerically pure compounds of indeterminate absolute configuration. Thus, for example, the formula X is intended to encompass both of the enantiomerically pure trans 1-amino-2-hydroxytetralins:

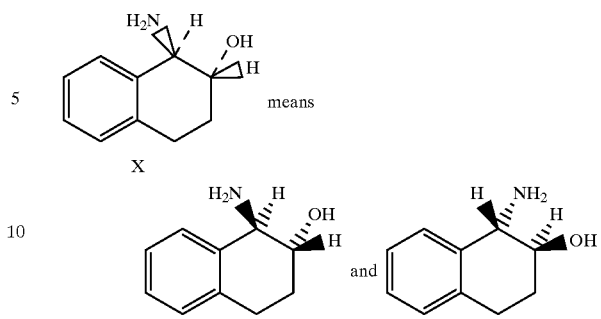

The term "enantiomeric excess" is well known in the art and is defined for a resolution of ab→a+b as $$ee_a = \left(\frac{\text{conc. of } a - \text{conc. of } b}{\text{conc. of } a + \text{conc. of } b}\right) \times 100$$

The term "enantiomeric excess" is related to the older term "optical purity" in that both are measures of the same phenomenon. The value of ee will be a number from 0 to 100, zero being racemic and 100 being pure, single enantiomer. A compound which in the past might have been called 98% optically pure is now more precisely described as 96% ee.; in other words, a 90% e.e. reflects the presence of 95% of one enantiomer and 5% of the other in the material in question. The term "diastereomeric excess (d.e.) is similarly defined as $$de_p = \left\{\frac{\text{conc. of } p - \text{conc. of } q}{\text{conc of } p + \text{conc of } q}\right\} \times 100$$

in which p and q are diastereomers, and 90% de reflects 95% of p and 5% of q. The diastereomeric excess is a measure of the diastereoselectivity of a reaction or process.

"Alkyl", as used herein, refers to saturated hydrocarbon residues containing twenty or fewer carbons in straight or branched chains, as well as cyclic structures. "Lower alkyl" is 6 or fewer carbons. "Alkoxy" refers to the same residues, containing, in addition, an oxygen atom at the point of attachment. "Aryl" includes phenyl, substituted phenyl, naphthyl and the like.

The processes of the invention are generically illustrated in Schemes 4 and 5. Scheme 4 depicts the process when the amino functionality of the aminoalcohol is not reactive with an activated acid, either by virtue of it being fully substituted or being rendered non-nucleophilic, e.g by formation of a sulfonamide. In this case, the hydroxyl of the aminoalcohol forms an ester with the carboxylic acid. Scheme 5 depicts the process when the amine is a primary amine and is thus capable of reacting with an activated carboxylic acid. In this case, the amine forms anamide with the carboxylic acid, and the hydroxyl, in the presence of an enol ether or a gem dialkoxyalkane, forms a 1,3-oxazolidine with the amine.

SCHEME 4

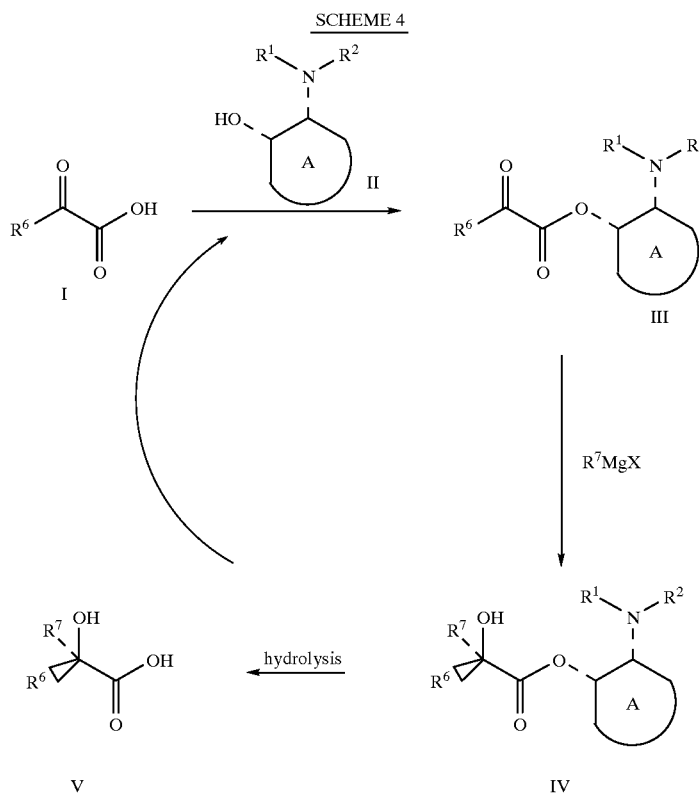

In Scheme 4, a pure enantiomer of a cis aminoalcohol II is shown for ease of understanding, but a pure enantiomer of a trans amino alcohol could also be used, and indeed many are disclosed below. $R^6$ is any residue that is unreactive towards a Grignard reagent, and $R^7$ is any residue that can form a Grignard reagent. Commonly, $R^6$ and $R^7$ are alkyl or aryl or alkyl or aryl substituted with one or more of alkoxy, alkyl or fluoroalkyl. In the examples below, $R^6$ and $R^7$ are phenyl and cyclohexyl. The acid I is shown as a free acid, but it will be apparent to the artisan that the acid could be in the form of an activated derivative, such as an acid chloride or anhydride.

The condensation of α-ketoacid I with cyclic 1,2-aminoalcohol II can be accomplished by any of the numerous ways known in the art for forming esters. For example, the α-ketoacid may be reacted with thionyl chloride or oxalyl chloride and the resulting the α-ketoacid chloride may then be reacted with the cyclic 1,2-aminoalcohol in the presence of a base to provide the aminoester III. Condensing agents for reacting the alcohol II with the acid I include carbodiimides of various sorts, mixed anhydrides, EEDQ, HATU, and the like. It is also possible to pre-react the carboxylic acid with an appropriate leaving group, so as to form an anhydride or, in some cases even an activated ester. Grignard addition to the chiral ester provides the CHPGA ester. By selecting chiral auxiliary and carrying the reaction under certain conditions, the Grignard reagent approaches the ketone functional group preferentially from one face, and selective addition takes place to yield α-hydroxyacid esters in high diastereomeric excess (d.e.). Hydrolysis of the ester provides the chiral (R or S) acid. Hydrolysis may be carried out conventionally with aqueous base or with any of the well known enzymes that are commercially available, particularly the lipase class of esterases.

Two preferred embodiments provide CHPGA via complementary routes. In the first embodiment, phenylglyoxylic acid is reacted with a single enantiomer of a vicinal aminoalcohol derivative of cyclopentane, cyclohexane, cycloheptane, indane, tetralin or benzosuberane to form an ester of the phenylglyoxylic acid; the ester is reacted with an excess of cyclohexylmagnesium bromide in an ethereal solvent, optionally in the presence of a zinc salt, at 20° to −78° C. to provide a reaction mixture containing an α-cyclohexylphenylglycolate ester; and a single diastereomer of α-cyclohexylphenylglycolate ester is separated from the reaction mixture. In the second route, a cyclohexylglyoxylic acid is reacted with a single enantiomer of a vicinal aminoalcohol derivative of cyclopentane, cyclohexane, cycloheptane, indane, tetralin or benzosuberane to form an ester of the cyclohexylglyoxylic acid; the ester is reacted with an excess of phenylmagnesium bromide in an ethereal solvent at 20° to −78° C. to provide a reaction mixture containing an α-cyclohexylphenylglycolate ester; and a single diastereomer of α-cyclohexylphenylglycolate ester is separated from the reaction mixture. In both cases the single diastereomer of α-cyclohexylphenylglycolate ester is hydrolyzed to provide α-cyclohexylphenylglycolic acid or an α-cyclohexylphenylglycolate salt enriched in one enantiomer.

As is well known in the art, Grignard reactions are commonly carried out in so-called "ethereal solvents". By this is meant that the solvent contains at least one C—O—C bond. Typical ethereal solvents include diethyl ether, methyl t-butyl ether, tetrahydrofuran (THF), dioxane, glyme (dimethoxyethane) and the like.

The N-substituted chiral aminoalcohols used in the synthesis are readily prepared from the corresponding aminoalcohol by tosylation or alkylation. Treatment of the chiral aminoalcohols with toluenesulfonyl chloride in dichloromethane in the presence of triethylamine (3 eq) for 3 h, provides N-tosylaminoalcohols in 70–90% yield. The starting aminoalcohols are commercially available or are prepared via Jacobson oxidation, Sharpless dihydroxylation and Jacobson ring-opening technology, followed by Ritter Reaction. The benzosuberane aminoalcohols, for example, are prepared in this fashion from benzocycloheptene, respectively. Syntheses of individual enantiomers of cyclic aminoalcohols are described in U.S. Pat. Nos. 5,516,943 and 5,677,469, and in Senanayake et al. *Tetrahedron Letters* 36, 7615–7618 (1995), the disclosures of which are incorporated herein by reference. The N-methylaminoindanol is prepared in two steps. Formylation of the cis-aminoindanol with formic acid gives the formyl amide in 85% yield. The amide is then reacted with borane in THF under reflux to give the N-methyl aminoindanol in 75% yield. N,N-Disubstituted aminoindanol is prepared by treatment of the cis-aminoindanol with formic acid and formaldehyde at 70° C. for 12 h. Some of the chiral auxiliaries prepared are shown in FIG. 2. Their antipodes can be similarly prepared in the fashion described above.

Figure 2

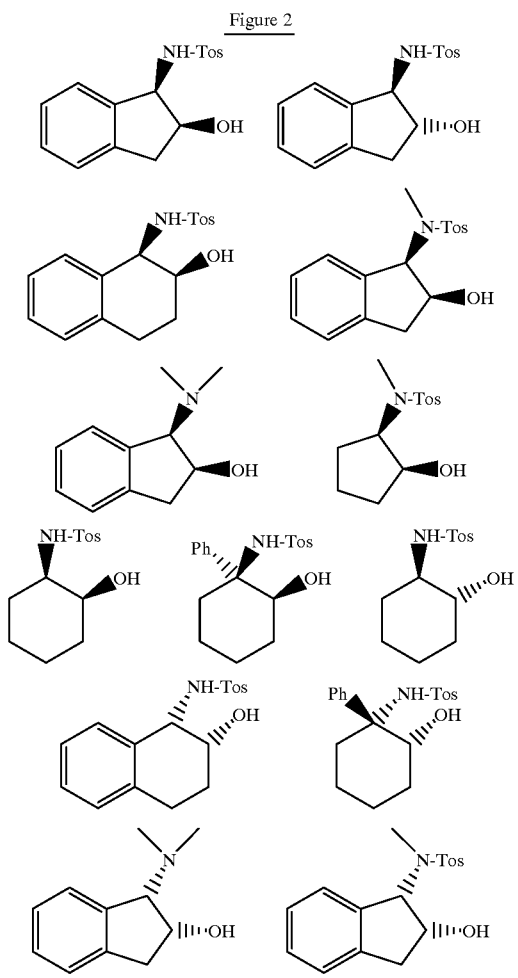

Compounds in which $R^1$ and $R^2$ taken together are phthaloyl or oxoisoindoline are prepared by treating the appropriate aminoalcohol with phthalic anhydride or methyl 2-(bromomethyl) benzoate, respectively.

Reaction of these aminoalcohols with phenylglyoxylic acid in the presence of DCC provides the corresponding esters. Alternatively, benzoylformic acid (or cyclohexylglyoxylic acid) is first treated with 1.5 equivalents of thionyl chloride at 70° C. for 1–2 h (or oxalyl chloride at 0° C. for 3 h) to give the acid chloride. The acid chloride is then reacted with the aminoalcohols to give the esters in 70–90% yields.

Cyclohexylglyoxylic acid is prepared by Grignard addition of cyclohexyl magnesium chloride to diethyl oxalate in 80–87% yield. Hydrolysis of the ester with NaOH yields the acid. The acid is converted to its chloride by treating with oxalyl chloride in dichloromethane at 0–15° C., and the crude acid chloride is reacted with tosylaminoindanol in dichloromethane at 0° C. to provide the ester in 73% yield after silica gel flash chromatography.

A number of chiral esters of phenylglyoxylic acid were dissolved in THF and added to a solution of cyclohexylmagnesium chloride and $ZnCl_2$ (ratio ca 1:1) at −78° C. (substrate: Grignard=1:3.5). After the addition, the reaction mixture was stirred for 30 min at that temperature and was warmed to rt and stirred for 2–12 h. The diastereomeric ratios of the products ranged from 1:1 to 6.6:1. Purification by crystallization or flash column chromatography of the crude product yielded a single diastereomer of the chiral CHPGA ester. When the order was reversed, i.e. phenyl Grignard was reacted with the cyclohexyl glyoxylate, and the reaction carried out in the absence of $ZnCl_2$, the d.e was very high. Results are shown in Table 1:

TABLE 1

| $R^1$ | $R^2$ | A | $R^6$ | $R^7$ | diastereomer ratio |
|---|---|---|---|---|---|
| tosyl | H | cyclohexyl(1S, 2S) | phenyl | cyclohexyl | 5.6:1 |
| tosyl | H | indanyl(1R, 2R) | phenyl | cyclohexyl | 6.6:1 |
| tosyl | H | tetralinyl(1R, 2S) | phenyl | cyclohexyl | 6:1 |
| tosyl | H | 2-phenyl-cyclohexyl(1S, 2R) | phenyl | cyclohexyl | 6.6:1 |
| tosyl | methyl | indanyl(1R, 2S) | phenyl | cyclohexyl | 4:1 |
| methyl | methyl | indanyl(1R, 2S) | phenyl | cyclohexyl | 5.2:1 |
| tosyl | H | indanyl(1R, 2S) | phenyl | cyclohexyl | 5:1 |
| tosyl | H | indanyl(1S, 2R) | cyclohexyl | phenyl | >49:1 |

When treated with sodium hydroxide in a water-methanol mixture, the ester from the Grignard addition gives the chiral CHPGA without racemization in 76% yield at 70° C.; in addition, the chiral auxiliary aminoalcohol (N-tosylaminoindanol) is recovered in 85% yield, as indicated in Scheme 4. The ability to recover the auxiliary in high yield is an advantageous feature of the process of the invention. It greatly reduces cost by allowing recycling of the auxiliary reagent.

A variant of scheme 4 in which the aminoalcohol carries a primary amine is shown in Scheme 5:

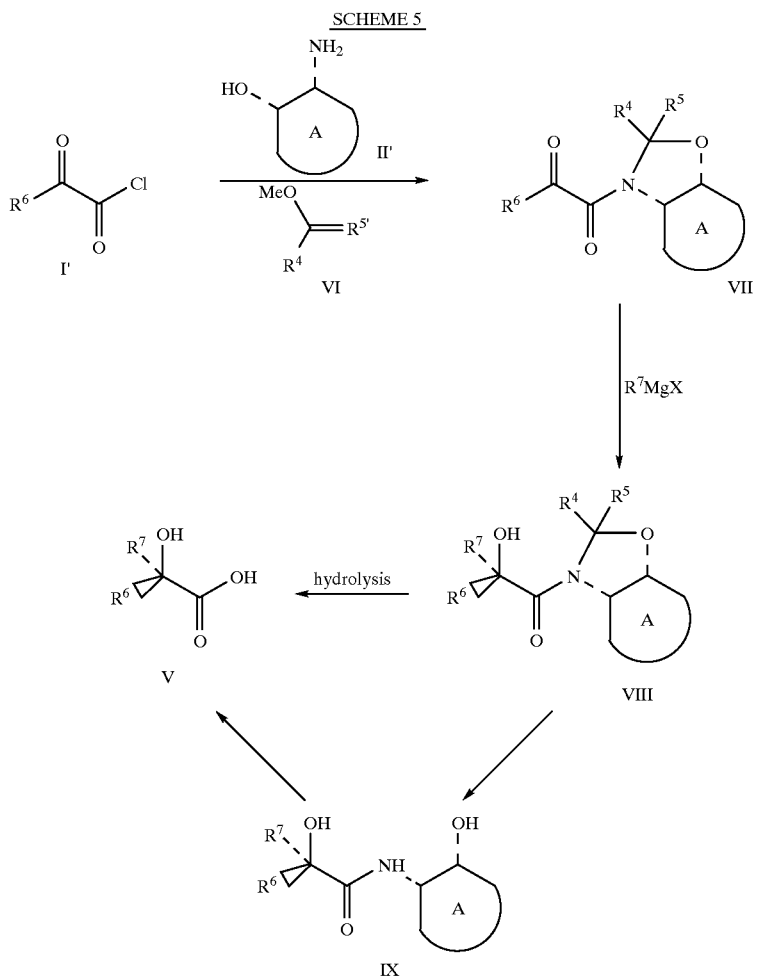

SCHEME 5

In the process shown in Scheme 5, an acid chloride of a prochiral α-ketocarboxylic acid I' is reacted with a single enantiomer of a vicinal aminoalcohol II' of cyclopentane, cyclohexane, cycloheptane, indane, tetralin or benzosuberane in the presence of an enol ether of a lower alkylketone VI and a strong organic acid or anhydrous Lewis acid catalyst. Alternatively, the acid chloride may be reacted with the aminoalcohol in the presence of a gem-dialkoxyalkane, such as 2,2-dimethoxypropane, and a strong organic acid or anhydrous Lewis acid catalyst. In either case, a 2,2-dialkyl-1-glyoxylyloxazolidine VII is formed. Typical catalysts include pyridinium toluenesulfonate, toluenesulfonic acid, methanesulfonic acid, scandium triflate, boron trifluoride etherate and the like. In the enol ether, $R^{5'}$ represents the remainder of residue $R^5$ in which the first methylene is incorporated into the enol. The 2,2-dialkyl-1-glyoxylyloxazolidine is reacted as before with an excess of a Grignard reagent in an ethereal solvent at 20° to −78 ° C. to provide a reaction mixture containing a 2,2-dialkyl-1-(β-hydroxy-α-oxomethyl)oxazolidine VIII; a single diastereomer of 2,2-dialkyl-1-(β-hydroxy-α-oxomethyl)oxazolidine is isolated from the reaction mixture; and the 2,2-dialkyl-1-(β-hydroxy-α-oxomethyl)oxazolidine is hydrolyzed to provide an α-hydroxycarboxylic acid or α-hydroxycarboxylate salt enriched in one enantiomer. As shown, the hydrolysis may be carried out in two steps: the first with aqueous mineral acid to cleave the oxazolidine (to give IX) and the second with alkali metal hydroxide in a high boiling solvent to cleave the amide (to give V). Alternatively, the second step may be accomplished enzymically. Suitable enzymes include lipases, such as Chiralzyme L-1™, Chiralzyme L-6™, 305™ (all available from Boehringer-Mannheim), Chiroclec PC™, Pepticlec™ (available from Altus Biologics) and AK™ (available from Amano); proteases such as Maxatase™ (available from Gist Brocades) and amide hydrolases, such as lysozyme (from Nagase). In preferred embodiments, the prochiral α-ketocarboxylic acid is phenylglyoxylic acid or cyclohexylglyoxylic acid and the vicinal aminoalcohol is 2-amino-1-cyclopentanol, 1-amino-2-tetralinol or 1-amino-2-indanol. In most cases the optimal enol ether is 2-methoxypropene. A typical acid catalyst is methansulfonic acid or toluenesulfonic acid, and the Grignard reagent is an arylmagnesium halide or cyclohexylmagnesium halide.

Although this invention is susceptible to embodiment in many different forms, preferred embodiments of the invention are shown below. It should be understood, however, that the present disclosure is to be considered as an exemplification of the principles of this invention and is not intended to limit the invention to the embodiments illustrated.

ABBREVIATIONS AND DEFINITIONS

The following is a dictionary of abbreviations and terms. All of them do not necessarily appear in the text:
Ac=acetyl
Boc=t-butyloxy carbonyl
Bu=butyl
c-=cyclo
DBU=diazabicyclo[5.4.0]undec-7-ene
DCM=dichloromethane=methylene chloride=$CH_2Cl_2$
DCC=dicyclohexylcarbodiimide
DIC=diisopropylcarbodiimide
DIEA=diisopropylethyl amine
DMAP=4-N,N-dimethylaminopyridine
DMF=N,N-dimethylformamide
DMSO=dimethyl sulfoxide
DVB=1,4-divinylbenzene
EEDQ=2-ethoxy-1-ethoxycarbonyl-1,2-dihydroquinoline
EtOAc=ethyl acetate
Fmoc=9-fluorenylmethoxycarbonyl
GC=gas chromatography
HATU=O-(7-Azabenzotriazol-1-yl)-1,1,3,3-tetramethyluronium hexafluorophosphate
HOAc=acetic acid
HOBt=hydroxybenzotriazole
Me=methyl
mesyl=methanesulfonyl
NMO=N-methylmorpholine oxide
PEG=polyethylene glycol
Ph=phenyl
PhOH=phenol
PfP=pentafluorophenol
PyBroP=bromo-tris-pyrrolidino-phosphonium hexafluorophosphate
rt=room temperature
sat'd=saturated
s-=secondary
t-=tertiary
TBDMS=t-butyldimethylsilyl
TFA=trifluoroacetic acid
THF=tetrahydrofuran
TMS=trimethylsilyl
Ts or Tos=tosyl=p-toluenesulfonyl
Trt=triphenylmethyl

EXPERIMENTAL DETAILS (EXAMPLES).

Aminoalcohol Chiral Auxiliary Preparation:

N-tosyl-cis-(1R, 2S)-aminoindanol: To a suspension of cis-(1R, 2S)-aminoindanol (14.9 g, 0.1 mol) in dichloromethane (400 mL) at 0° C. was added triethylamine (20 mL), followed by addition of TsCl (18.5 g, 0.1 mol). The reaction mixture was stirred for 30 min at rt and washed with water (2×100 mL), dried with sodium sulfate, and filtered. The filtrate was then concentrated to remove most of the solvent, followed by addition of hexane (150 mL). The solids formed were collected by filtration and dried to give 26 g (yield 98%). Similarly, N-tosyl-cis-(1S,2R)-aminoindanol (its enantiomer) was prepared starting with the (1S,2R)-isomer of aminoindanol. $^1$H NMR (CDCl$_3$) δ 2.05 (broad s, 1H), 2.46 (s, 3H), 2.82–2.88 (d, J=16 Hz, 2.95–3.06 (dd, J1=Hz, J2=16 Hz, 1H), 4.30 (m, 1H), 4.66 (m, 1H), 5.40 (m, 1H), 7.04–7.20 (m, 4H), 7.32–7.36 (d, J=8 Hz, 2H), 7.84–7.90 (d, J=8 Hz, 2H). $^{13}$C-NMR δ 21.51, 39.14, 61.18, 72.76, 124.44, 125.23, 127.03, 127.14, 128.34, 129.75, 137.47, 139.40, 143.64.

N-Tosyl-trans-(1R, 2R)-aminoindanol: By using the same tosylation procedure (yield 86%): $^1$H NMR (CDCl$_3$) δ 2.40 (s, 3H), 2.55 (m, 1H), 2.80 (m, 1H), 3.20 (m, 1H), 3.8–4.6 (broad s, 1H), 4.44 (s, 2H), 6.90 (d, J=4 Hz, 1H), 7.10–7.30 (m, 4H), 7.36–7.39 (d, J=6 Hz, 1H), 7.88–7.96 (d, J=6 Hz, 2H)

N-Tosyl-trans (1R, 2R)-cyclohexylaminoalcohol: $^1$H NMR (CDCl$_3$) δ 1.00–1.20 (m, 4H), 1.5–1.8 (m, 3H), 2.00 (m, 1H), 2.44 (s, 3H), 2.7–2.95 (m, 2H), 3.22–3.35 (m, 1H), 4.80 (broad s, 1H), 7.25–7.28 (d, J=7.5 Hz, 2H), 7.77–7.80 (d, J=7.5 Hz, 2H).

N-Methyl-N-tosyl-(1R, 2S)-aminoindanol (89% yield): 1H NMR (CDCl$_3$) δ 2.47 (s, 3H), 2.69 (s, 3H), 2.87–2.94 (d,d, J1=5.1 Hz, J2=16.5 Hz, 1H), 3.17–3.25 (d,d, J1=7.2 Hz, J2=16.8 Hz, 1H), 4.67–4.71 (m, 1H), 5.23–5.29 (m, 1H), 6.39–6.42 (d, J=4.6 Hz, 1H), 7.05 (m, 1H), 7.22 (m, 2H), 7.36–7.39 (d, J=8.1 Hz, 2H), 7.81–7.84 (d, J=8.1 Hz, 2H). $^{13}$C (75 MHZ) 6 21.56, 32.38, 39.56, 64.22, 72.88, 125.31, 125.47, 126.96, 127.17, 128.81, 129.86, 16.58, 136.70, 140.85, 143.64.

N,N-Dimethyl-cis-(1R,2S)-aminoindanol: Cis-(1R, 2S)-aminoindanol (5 g) was dissolved in aqueous formaldehyde (18 mL) and formic acid (10 mL). The reaction mixture was heated to 70° C. for 40 h, and cooled to rt, suspended in ethyl acetate (60 mL) and added potassium carbonate till basic, the organic phase was separated and washed with brine, dried with sodium sulfate, and filtered to remove the drying agent. The filtrate was concentrated to give the oil, which was solidified on standing (4.5 g, 76% ). $^1$H NMR (CDCl$_3$) δ 2.25 (s, 6H), 2.80 (m, 1H), 3.24 (m, 1H), 4.06 (d, J=6 Hz, 1H), 4.42 (m, 1H), 4.20–4.60 (broad s, 1H), 7.17–7.38 (m, 4H). $^{13}$C (75 MHZ) δ 41.24, 43.15, 69.54, 69.74, 125.51, 126.33, 126.39, 128.50, 138.33, 141.62.

N-methyl-cis-(1R,2S)-aminoindanol: cis-(1R,2S)-aminoindanol (14.9 g) was suspended in toluene (250 mL), followed by addition of formic acid (6 mL). The reaction mixture was heated at reflux for 3 h, then distilled off toluene (60 mL). The residue was then cooled to −10° C., the precipitate was collected by filtration and dried to give 15 g formyl amide intermediate. The intermediate (14 g) was suspended in THF (250 mL) and BH$_3$Me$_2$S (10 M, 12 mL) was added in 5 min cooling with ice-water bath. After the addition, the reaction mixture was heated at reflux for 4 h and stirred at 60° C. for 60 h. The solution was then cooled to 0° C., quenched with methanol (100 mL), and concentrated to give a white solid residue. The solid was suspended in methanol (100 mL) and concentrated again. The residue solid was then suspended in ethyl acetate (200 mL) and followed by an usual aqueous workup to give 12.5 g (94% yield). $^1$H NMR (CDCl$_3$) δ 2.60 (s, 3H), 2.4–2.9 (broad s, 2H), 2.93–3.10 (m, 2H), 3.94–3.96 (d, J=5.1 Hz, 1H), 4.40–4.47 (m, 1H), 7.23 (m, 4H). $^{13}$C (75 MHZ) δ 35.19, 39.62, 67.63, 70.25, 123.64, 125.65, 126.63, 128.02, 141.11, 142.03.

Substrate Preparation:

N,N-Dimethyl-cis-(1R, 2S)-1-aminoindanyl phenylglyoxylate (general method 1 via DCC coupling): To a solution of phenylglyoxylic acid (1.1 g) in dichloromethane (20 mL) was added DCC (1.65 g), DMAP (0.5 g) and N,N-Dimethyl-cis-(1R, 2S)-1-aminoindanol (1.1 g). The reaction mixture was stirred for 20 h at rt, filtered through Celite and concentrated to give an oil. The product was isolated by silica gel column chromatography (EtOAc:Hex=3:7) to give a colorless oil. $^1$H NMR (CDCl$_3$) δ 2.30 (s, 6H), 3.20–3.40 (m, 2H), 4.58 (d, J=7 Hz, 1H), 5.72 (m, 1H), 7.23–7.66 (m, 7H), 8.20 (d, J=7.5 Hz). $^{13}$C (75 MHZ) δ 37.11, 41.79, 67.66, 76.91, 124.95, 126.15, 126.94, 128.45, 128.71, 130.34, 132.52, 134.77, 138.30, 139.02, 164.00, 186.89.

Cis-(1R, 2S)-1-tosylaminoindanyl phenylglyoxylate (general method 2 via phenylglyoxyl chloride): Phenylglyoxylic acid (41 g, 0.27 mol) was added thionyl chloride (41 mL), and heated to 70–75° C. for 2 h. The reaction mixture was then concentrated to remove excess thionyl chloride. The residue was then dissolved in dichloromethane (100 mL), and added to a solution of N-tosyl-cis-(1R, 2S)-aminoindanol (60 g, 0.2 mol), and triethylamine (30 mL) in dichloromethane (800 mL) at 0° C. over a period of 5 min. The reaction mixture was stirred for 15 min. and washed with water (300 mL), 10% acetic acid (2×100 mL), and water (300 mL), and dried with sodium sulfate. The drying agent was removed by filtration, the filtrate was concentrated to ca 50 mL, followed by addition of a mixture of ethyl acetate and hexane (3:7, 400 mL). White precipitate was collected by filtration, dried to give 58 g product (67%). $^1$H NMR δ 2.39 (s, 3H), 3.05–3.11 (d, J=17.4 Hz, 1H), 3.19–3.27 (d,d, J1=17.4 Hz, J2 =4.8 Hz), 1H), 5.08–5.14 (m, 1H), 5.30–5.33 (d, J=10.5 Hz, 1H), 5.43–5.46 (m, 1H), 7.18–7.30 (m, 6H), 7.45–7.50 (m, 2H), 7.61–7.66 (m, 1H), 7.83–7.86 (d, J=8.4 Hz, 2H), 7.92–7.95 (d, J=8.4 Hz, 2H). $^{13}$C-NMR δ 21.39, 37.11, 59.62, 77.13, 124.04, 124.89, 126.88, 127.41, 128.64, 128.76, 129.79, 129.95, 131.90, 134.91, 137.55, 137.99, 138.99, 143.66, 162.26, 185.03.

Cis-(1R, 2S)-1-N-tosyl-N-methyl-aminoindanyl phenylglyoxylate (method 2): except that the final product as thick oil by silica gel chromatography using ethyl acetate:hexane (3:7) as eluate (77%). $^1$H NMR 2.33 (s, 3H), 2.69 (s, 3H), 3.08–3.15 (dd, J1=3 Hz, J2=17.4 Hz, 1H), 3.32–3.40 (dd, J1=6.6 Hz, J2=17.4 Hz), 5.76–5.78 (d, J=6.3 Hz, 1H), 5.86 (m, 1H), 6.68–6.70 (d, J=7.5 Hz, 1H), 7.10–7.18 (m, 1H), 7.24–7.28 (m, 5H), 7.48–7.54 (m, 2H), 7.63–7.68 (m, 1H), 7.77–7.80 (d, J=8.1 Hz), 8.01–8.04 (d, J=8.1 Hz, 2H). $^{13}$C-NMR δ 21.37, 32.20, 37,54, 62.86, 76.91, 124.81, 125.28, 127.08, 127.43, 128.83, 129.74, 130.18, 132.14, 134.91, 136.56, 138.87, 143.45, 162.18, 184.86.

Trans-(1R, 2R)-2-Tosylaminocyclohexyl phenylglyoxylate (method 2): It was isolated by flash chromatography (EtOAc:Hexane=3:7) in 75% yield. $^1$HNMR, δ 1.23–1.38 (m, 3H), 1.42–1.56 (m, 1H), 1.58–1.68 (m, 1H), 1.70–1.78 (m, 1H), 1.94–2.02 (m, 1H), 2.08–2.20 (m, 1H), 2.29 (s, 3H), 3.30–3.42 (m, 1H), 4.80–4.92 (m, 1H), 5.00–5.03 (d, J=8.4 Hz, 1H), 7.08–7.11 (2H, d, J=8.7 Hz, 2H), 7.49–7.54 (m, 2H), 7.64–7.70 (m, 3H), 8.00–8.03 (m, 2H). $^{13}$C-NMR δ, 21.40, 23.41, 23.90, 30.65, 32.84, 56.12, 76.35, 126.80, 128.85, 129.60, 130.22, 132.23, 134.86, 137.91, 143.24, 163.48, 185.57.

Cis-1,2,3,4-tetrahydro-1-Tosylamino-naphthyl phenylglyoxylate (method 2): $^1$H NMR, δ 1.93–2.10 (m, 1H), 2.37–2.40 (m, 1H), 2.39 (s, 3H), 2.70–2.80 (m, 1H), 2.86–3.00 (m, 1H). 4.84 (m, 1H), 5.04 (m, 1H), 5,30 (m, 1H), 7.05–7.30 (m, 6H), 7.46–7.54 (m, 2H), 7.62–7.68 (m, 1H), 7.78–7.83 (m, 2H), 7.93–7.98 (M, 2H). $^{13}$C-NMR δ, 21.51, 24.30, 24.87, 53.68, 72.91, 126.77, 126.88, 127.93, 128.16, 128.71, 128.93, 129.86, 130.03, 132.15, 132.93, 135.01, 135.72, 138.05, 143.68, 163.09, 185.47.

Cyclohexylglyoxylate Preparation:.

Synthesis of Ethyl cyclohexyloxoacetate: Cyclohexyl magnesium bromide (Aldrich) in ether (2 M, 150 mL) was pumped under vacuum to remove ethyl ether, at rt, the residue obtained was then dissolved in anhydrous THF (100 mL) while cooled with an ice water bath. The solution was then added to a solution of diethyl oxalate (60 g) in THF (150 mL) at −30—40° C. in 10 min. The reaction mixture was warmed to 0° C. for 5 min, and quenched with 10% HCl (100 mL), extracted with ethyl acetate (200 mL), the extract was washed with water (30 mL), brine (50 mL) and dried with sodium sulfate, then filtered. The filtrate was concentrated to give an oil. It was distilled 40–50° C. at 1 mm Hg to remove the starting material and the left over is the product (total of 46 g, 86% yield, purity>90%, it can be distilled at 1 mm Hg, 75–80° C.): $^1$H NMR δ 1.20–1.40 (m, 8H), 1.62–1.94 (m, 5H), 3.02 (broad s, 1H), 4.30 (q, J=8 Hz, 2H). $^{13}$C-NMR δ 13.91, 25.11, 25.58, 27.36, 46.13, 62.07, 161.84, 197.51.

Synthesis of cyclohexylglyoxylic acid: To a solution of ethyl cyclohexyloxoacetate (46 g) in MeOH (25 mL) was added water (60 mL) and NaOH (50% 20 mL) at 0–15° C. The reaction mixture was heated to 60° C. for 1.5 h. The reaction mixture was cooled with ice-water bath, and acidified with 15% HCl till pH 1. The mixture was extracted with ethyl acetate (2×250 mL). The extracts were washed with brine, dried with sodium sulfate. The drying agent was removed by filtration and the solvent was removed to give a low melting solid (39 g, 99%). $^1$H NMR: δ 1.15–1.40 (m, 5H,), 1.62–1.96 (m, 5H). 3.20 (m, 1H), 9.4 (s, 1H). $^{13}$C-NMR δ 25.93, 25.76, 27.89, 45.04, 160.90, 198.29.

Synthesis of cis-(1S, 2R)-1-tosylaminoindanyl cyclohexyloxylate: To a solution of cyclohexyloxylic acid (4.7 g) in dichloromethane (30 mL) at 0° C. was added oxalyl chloride (4.0 mL), followed by addition of 1 drop of DMF. The reaction mixture was stirred at 0° C. for 3 h, followed by the removal of solvent. The residue was then dissolved in dichloromethane (30 mL) to give total volume of 34 mL. Total of 22 mL of the solution was then added to a solution of cis-(1S, 2R)-N-tosylaminoindanol (4.5 g, 15 mmol) and triethyl amine (3.2 mL) in dichloromethane (50 mL) at 0° C. The reaction mixture was then concentrated to remove dichloromethane, the resulting residue was then dissolved in ethyl acetate (50 mL), washed the solution with water (30 mL), and 1% HCl (20 mL), water (20 mL), and dried with sodium sulfate. The drying agent was removed by filtration and the filtrate was concentrated to give a foaming solid. the product was isolated by flash chromatography using ethyl acetate and hexane (3:7) to give 4.7 g solid in 72% yield. $^1$H NMR. δ 1.15–1.36 (m, 5H), 1.56–1.80 (m, 5H), 2.46 (s, 3H), 2.82 (m, 1H). $^{13}$C NMR δ 21.44, 25.07, 25.48, 27.31, 37.03, 46.09, 59.60, 76.42, 124.14, 124.85, 126.89, 127.46, 128.69, 129.70, 137.67, 137.93, 138.99, 143.64, 160.48, 196.27. M+(440)

Grignard Addition to the Substrate:

Phenyl Grignard addition to cis-(1S, 2R)-1-tosylaminoindanyl cyclohexyloxylate: To a solution of phenyl Grignard (3 M 23 mL) in THF (60 mL) was added cis-(1S, 2R)-1-tosylaminoindanyl cyclohexyloxylate (10 g, 22 mmol) in THF (60 mL) at 0° C. over a period of 5 min. The reaction mixture was then stirred for 15 min, followed by addition of 10% HCl (20 mL). The reaction mixture was then added water (20 mL), extracted with ethyl acetate (60 mL). The extract was washed with water (30 mL), brine (40 mL), and concentrated to give an oil, which was purified by crystallization with ethyl acetate and hexane to give to give the product (9.2 g, 77% yield). $^1$H NMR δ 0.92–1.16 (m, 4H), 1.28–1.28–1.43 (m, 2H), 1.44–1.54 (m, 1H), 1.54–1.68 (m, 2H), 1.78–1.88 (m, 1H), 1.95–2.04 (m, 1H), 2.43 (s, 3H), 2.53–2.58 (d, J=17.4 Hz, 1H), 2.93–2.30 (d, d, J1=4.5 Hz, J2=17.4 Hz), 3.51 (s, 1H), 4.99–5.04 (m, 1H), 5.12–5.16 (d, J=10.5 Hz, 1H), 5.23–5.56 (m, 1H), 6.96–7.20 (m, 4H), 7.21–7.38 (m, 7H), 7.76–7.79 (d, J=8.4 Hz, 2H). $^{13}$C-NMR δ 21.56, 25.30, 26.06, 26.31, 27.55, 36.87, 45.87, 59.62, 78.00, 81.32, 123.97, 125.01, 125.54, 126.93, 127.32, 127.51, 127.94, 128.66, 129.88, 137.49, 138.31, 140.03, 143.89, 174.56. Mass. M+519.

Cyclohexyl Grignard addition to cis-(1R, 2S)-1-tosylaminoindanyl phenylgloxylate (ZnCl$_2$ catalyzed): Cyclohexyl magnesium chloride (2 M, 50 mL, 0.1 mol) was added to a solution of ZnCl₂ (1 M, 80 mL, 0.08 mol) in ethyl ether at 0° C. over a period of 3 min. The reaction mixture was cooled to −78° C., followed by addition of cis-(1R, 2S)-1-tosylaminoindanyl phenylglyoxylate (8.6 g, 0.02 mol) in THF (50 mL). The reaction mixture was then warmed to rt, stirred for 1 h, and quenched with ammonium chloride solution (40 mL), followed by addition of ethyl acetate (100 mL), water (150 mL) and 10% HCl (40 mL). The organic phase was separated, aqueous phase was extracted with ethyl acetate (150 mL), the organic phases were combined and washed with water (100 mL), brine (30 mL), and dried over sodium sulfate. The drying agent was removed by filtration, and the filtrate was concentrated to give 9 g crude product with de of (85:15). The crude product was crystallized ethyl acetate and hexane (2:3, 100 mL) to give 5.6 g (55%) diastereomerically pure product. ¹H NMR δ 0.80–1.10 (m, 4H), 1.12–1.40 (m, 3H), 1.50–1.63 (m, 2H), 1.62–1.73 (m, 1H), 1.85–1.95 (m, 1H), 2.40 (s, 3H), 2.85–3.10 (m, 2H), 3.64 (s, 1H), 4.48–4.52 (d, J=10.5 Hz, 1H), 4.80 (m, 1H), 4.87–4.92 (m, 1H), 7.02–7.12 (m, 4H), 7.18–7.52 (m, 9H). 13C-NMR d≡21.50, 25.26, 25.94, 26.82, 37.00, 44.48, 59.99, 77.31, 80.46, 124.22, 124.67, 125.84, 126.53, 127.58, 128.23, 128.63, 128.82, 129.64, 137.24, 137.72, 139.36, 140.44, 143.55, 174.40.

Chiral CHPGA Preparation (Base Hydrolysis).

General Procedure for the hydrolysis of CHPGA esters: To suspension of cis-(1S, 2R)-1-tosylaminoindanyl (S)-cyclohexylmandalate (1.04 g) in water (10 mL) and methanol(10 mL) was added 50% sodium hydroxide (0.8 mL). The reaction mixture was heated to 70–80° C. for 2 h, cooled to rt, and added HCl (6N) till neutral pH, followed by addition of potassium carbonate (10 mL) till pH 10–11. The precipitate was formed and was collected by filtration to give the crude ligand (0.8 g). The filtrate was extracted with ethyl acetate (5 mL). the aqueous phase was then acidified with 6N HCl till pH 1, then extracted with ethyl acetate (40 mL). The extract was washed with brine and concentrated to give 350 mg product with 98% ee. ¹H NMR δ 1.00–1.50 (m, 6H), 1.66 (m, 3H), 1.8 (m, 1H), 2.24 (m, 1H), 3.40 (broad s, 1H), 7.20–7.40 (m, 3H), 7.60–7.65 (d, J=2H), 10.0 (broad s, 1H). ¹³C-NMR δ 25.40, 26.10, 26.24, 27.36, 45.67, 80.99, 125.92, 127.70, 128.18, 139.82, 180.80. M+(234).

Oxazolidine Route (Scheme 5)

Preparation of oxazolidine VII (R⁴=R⁵=methyl; R⁶=phenyl; A=indane): A solution of (1S,2R)-1-aminoindanol-2-ol (14.9 g, 100.0 mmol) in 220 ml of dry THF and triethylamine (14.57 ml, 104.8 mmol) in a 500 mL round bottom flask equipped with a thermocouple probe, mechanical stirrer, and a nitrogen inlet adapter and bubbler, was cooled to 0° C. Then benzoylformoyl chloride I' (16.8 g, 100.0 mmol) was added over 15 min. After addition, the mixture was allowed to warm to rt and stirred for an additional 30 min. The reaction was treated with pyridinium p-toluenesulfonate (4.0 g, 16.0 mmol) and stirred for 10 minutes. Then, 2-methoxypropene (21.0 mL, 223 mmol) was added and reaction was heated to 40° C. for 5 h. The reaction mixture was cooled to 20° C., and partitioned with ethyl acetate (150 mL) and 5% aqueous NaHCO₃ (125 mL). The mixture was agitated and the layers were separated. The ethyl acetate extract was concentrated in vacuo. Cyclohexane (150 mL) was added to the oil and the mixture was concentrated again in vacuo to provide crude product. The oil was chromatographed using 15% ethylacetate/hexane as eluent to provide 25.5 g (80%) of VII as an oil. ¹H NMR (CDCl₃, 300 MHZ) δ 8.10 (d, J=7 Hz, 1H), 7.68–7.10 (m, 8H), 5.35 (d, J=4 Hz, 1H), 4.89 (t, J=4Hz, 1H), 3.08 (m, 2H), 1.83 (s, 3H), 1.49 (s, 3H). ¹³C NMR (CDCl₃, 75 MHZ) 19.6, 22.1, 31.7, 61.1, 92.6, 121.0, 122.5, 122.8, 124.1, 125.3, 125.4, 130.1, 130.4, 135.5, 136.1, 158.9, 160.2.

Addition of Grignard to Prepare Oxazolidine VIII (R⁷= cyclohexyl): A solution of VII in dry THF (400 mL) was cooled to −78° C. and treated with cyclohexyl magnesium chloride (122.5 mL, 245 mmol, 2M solution in ether). The reaction was allowed to stir at −78° C. for 1 h and slowly warmed to rt and allowed to stir an additional 2 h. The reaction mixture was partitioned with water (400 mL) and ethyl acetate (400 mL). The layers were separated. The ethyl acetate layer was concentrated in vacuo and chromatographed using 10% ethylacetate/hexane as eluent to provide 14.7 g (52%) of VIII as a solid. ¹H NMR (CDCl₃, 300 MHZ) δ 7.61–7.21 (m, 9H), 5.68 (d, J=3 Hz, 1H), 4.32 (m, 1H), 3.00 (s, 2H), 2.68 (m, 1H), 2.21 (m, 1H), 1.97–1.09 (m, 10H), 1.49 (s, 3H), 1.30 (s, 3H). ¹³C NMR (CDCl₃, 75 MHZ) 9.8, 19.0, 21.8, 22.0, 22.5, 24.0, 31.7, 41.8, 56.0, 61.9, 75.0, 79.5, 93.6, 120.7, 120.9, 122.0, 122.2, 122.6, 123.7, 123.8, 136.2, 137.6, 138.0, 164.1.

Preparation of amide IX: Oxazolidine VIII (8.9 g, 21.9 mmol) was dissolved in 30 mL of THF and 30 mL of 6N HCl at rt. After stirring at rt for 2 h, the reaction was neutralized with 3N KOH solution and the volatiles were removed in vacuo. The reaction was partitioned with ethyl acetate (50 mL) and water (50 mL) and the ethyl acetate layer was concentrated in vacuo to provide 7.8 g of the amide (97%). ¹H NMR (CDCl₃, 300 MHZ) δ 7.44–6.88 (m, 9H), 5.29 (d, J=9 Hz, 1H), 4.51 (m, 1H), 3.12 (d, J=15 Hz, 1H), 2.92 (d, J=15 Hz, 1H), 2.48 (m, 1H), 1.91–0.97 (m, 10H). 13C NMR (CDCl₃, 75 MHz) 21.2, 21.8, 22.5, 35.2, 40.1, 52.7, 69.3, 77.6, 119.7, 120.7, 120.8, 120.9, 122.4, 123.7, 124.0, 135.4, 136.1, 137.2, 170.2.

Preparation of CHPGA (V): Adduct IX (287 mg, 0.76 mmol) was dissolved in 10 mL of ethylene glycol under argon and allowed to reflux for 24 h. The reaction was allowed to cool. It was partitioned between 100 mL of water and 100 mL of ethyl acetate. The ethyl acetate layer was concentrated in vacuo and chromatographed using 2% MeOH/EtOAc as eluent to provide chiral CHPGA in 52% yield.

We claim:
1. A compound of formula

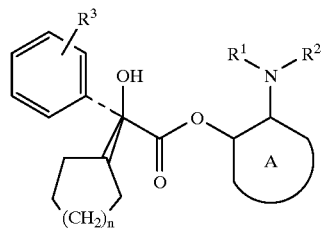

wherein
R¹ is chosen from the group of alkyl, cycloalkyl, and toluenesulfonyl;
R² is alkyl or cycloalkyl, or, when R¹ is toluenesulfonyl, R² may additionally be hydrogen; or together R¹ and R² are alkylene,

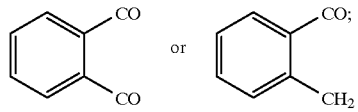

R³ is one or more substituents chosen independently from the group of hydrogen, alkyl, alkoxyl and halo;

n is 1, 2, 3 or 4; and

A is a cyclic residue chosen from the group of cis or trans cyclopentane, cyclohexane, cycloheptane, indane, tetralin and benzosuberane.

2. A compound of formula

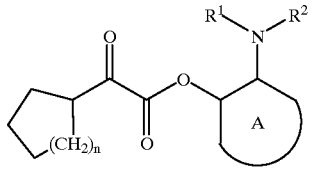

wherein $R^1$ is chosen from the group of alkyl, cycloalkyl, and toluenesulfonyl;

$R^2$ is alkyl or cycloalkyl, or, when $R^1$ is toluenesulfonyl, $R^2$ may additionally be hydrogen;

or together $R^1$ and $R^2$ are alkylene,

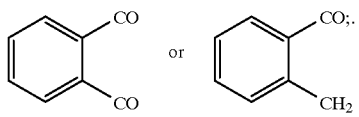

n is 1, 2, 3 or 4; and

A is a cyclic residue chosen from the group of cyclopentane, cyclohexane, cycloheptane, indane, tetralin or benzosuberane having a configuration such as to give rise to a single enantiomer or a mixture of enantiomers enriched in one enantiomer.

3. A compound according to claim 1 wherein $R^3$ is hydrogen.

4. A compound according to claim 2 or 3 wherein A is cyclopentane, cyclohexane, indane or tetralin.

5. A compound according to claim 3 wherein $R^1$ is toluenesulfonyl and $R^2$ is hydrogen.

6. A compound according to claim 3 wherein $R^1$ is toluenesulfonyl and $R^2$ is methyl.

7. A compound according to claim 3 wherein $R^1$ and $R^2$ are both methyl.

8. A compound according to claim 1 or 2 wherein A is indane.

9. A compound according to claim 8 wherein $R^1$ is toluenesulfonyl and $R^2$ and $R^3$ are hydrogen.

10. A compound according to claim 1 chosen from

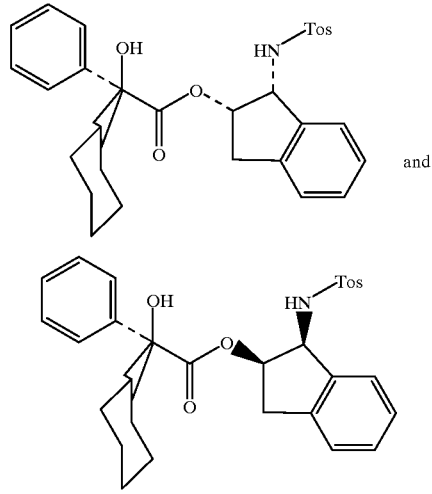

and

11. A compound according to claim 2 chosen from

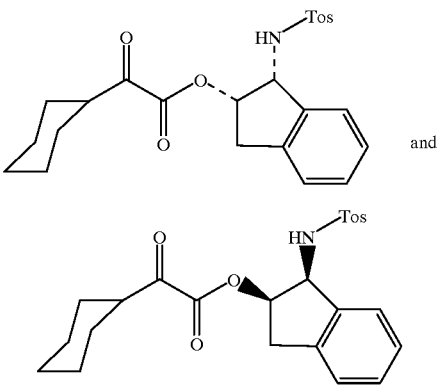

and

* * * * *